(12) United States Patent
Yokota et al.

(10) Patent No.: US 9,302,051 B2
(45) Date of Patent: Apr. 5, 2016

(54) INJECTION NEEDLE ASSEMBLY AND DRUG INJECTION DEVICE

(75) Inventors: Takayuki Yokota, Yamanashi (JP); Yoichiro Iwase, Ashigarakami-gun (JP); Naoki Sakaguchi, Ashigarakami-gun (JP); Kazunori Koiwai, Ashigarakami-gun (JP); Yoshinori Hishikawa, Yamanashi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 362 days.

(21) Appl. No.: 13/638,473

(22) PCT Filed: Mar. 2, 2011

(86) PCT No.: PCT/JP2011/054801
§ 371 (c)(1),
(2), (4) Date: Dec. 10, 2012

(87) PCT Pub. No.: WO2011/122221
PCT Pub. Date: Oct. 6, 2011

(65) Prior Publication Data
US 2013/0079729 A1    Mar. 28, 2013

(30) Foreign Application Priority Data

Mar. 31, 2010  (JP) ................................ 2010-082586

(51) Int. Cl.
*A61M 5/315*    (2006.01)
*A61M 5/31*    (2006.01)

(52) U.S. Cl.
CPC ......... *A61M 5/31511* (2013.01); *A61M 5/3129* (2013.01); *A61M 5/3135* (2013.01); *A61M 5/3137* (2013.01)

(58) Field of Classification Search
CPC .......... A61M 5/31511; A61M 5/3129; A61M 5/3135; A61M 5/3137
USPC .............. 604/27, 36, 38, 93.01, 181, 18, 214, 604/218, 222, 225
See application file for complete search history.

(56) References Cited

U.S. PATENT DOCUMENTS 5,330,430 A * 7/1994 Sullivan ................ A61M 5/326
                                                    604/134
5,435,076 A    7/1995 Hjertman et al.
(Continued)

FOREIGN PATENT DOCUMENTS

GB    2 437 924 A    11/2007
JP    5-7624 A    1/1993
(Continued)

OTHER PUBLICATIONS

European Search Report Dated Nov. 5, 2014, issued in application No. 11762461.9-1662.

*Primary Examiner* — Kevin C Sirmons
*Assistant Examiner* — Amber Stiles
(74) *Attorney, Agent, or Firm* — Sughrue Mion, PLLC

(57) ABSTRACT

A needle does not come off even if a high back pressure occurs at the skin upper section. Thus, the drug leakage from the skin can be prevented. A drug administration device 1 includes a tubular section 2 having a fluid chamber 7 capable of accommodating a drug and a discharge section 22, a pusher member 3 moving within the tubular section 2, a grip section 4, and a connection section 5. The pusher member 3 includes a rod-shape plunger 31 and a gasket 32. The grip section 4 is disposed along the outer periphery of the tubular section 2 and kept away from the tubular section 2, and the connection section 5 is formed between the tubular section 2 and the grip section 4.

11 Claims, 6 Drawing Sheets

(56) References Cited

U.S. PATENT DOCUMENTS

| | | | |
|---|---|---|---|
| 5,512,054 A * | 4/1996 | Morningstar | 604/191 |
| 6,004,296 A * | 12/1999 | Jansen et al. | 604/198 |
| 6,544,233 B1 * | 4/2003 | Fukui | A61M 5/31596 |
| | | | 604/191 |
| 2004/0030294 A1 | 2/2004 | Mahurkar | |
| 2006/0052747 A1 | 3/2006 | Nishimura et al. | |
| 2007/0060893 A1 | 3/2007 | Mahurkar | |
| 2008/0195059 A1 | 8/2008 | Sudo et al. | |
| 2009/0163867 A1 | 6/2009 | Marshall et al. | |
| 2011/0201999 A1 | 8/2011 | Cronenberg et al. | |

FOREIGN PATENT DOCUMENTS

| | | |
|---|---|---|
| JP | 7-51370 A | 2/1995 |
| JP | 7-246237 A | 9/1995 |
| JP | 2003-159328 A | 6/2003 |
| JP | 2003-164524 A | 6/2003 |
| JP | 2004-215783 A | 8/2004 |
| JP | 2004-261403 A | 9/2004 |
| JP | 2007-159717 A | 6/2007 |
| JP | 2008-194317 A | 8/2008 |
| WO | 93/20869 A1 | 10/1993 |
| WO | 2010/033806 A2 | 3/2010 |

* cited by examiner

INJECTION NEEDLE ASSEMBLY AND DRUG INJECTION DEVICE

CROSS REFERENCE TO RELATED APPLICATIONS

This application is a National Stage of International Application No. PCT/JP2011/054801 filed Mar. 2, 2011, claiming priority based on Japanese Patent Application No. 2010-082586 filed Mar. 31, 2010, the contents of all of which are incorporated herein by reference in their entirety.

TECHNICAL FIELD

This invention relates to a drug administration device and drug injection device that are improved in operability when used for drug administration in the body.

BACKGROUND ART

In general, where a drug is administered in the body, there is used a drug administration device (syringe) including an outer tube and a plunger. The plunger is so operated that the drug filled in a fluid chamber of the outer tube is discharged into the body through an injection needle connected to the tip of the outer tube.

The skin is made up of three layers including epidermis, dermis and subcutis. The epidermis is a layer having a thickness of about 50 to 200 μm from the skin surface and the dermis is an about 1.5 to 3.5 mm thick layer lying adjacent from the epidermis. Since an influenza vaccine is generally subjected to subcutaneous or intramuscular administration, it is administered in the lower region of the skin or a deeper section thereof.

On the other hand, in order to reduce an injected quantity of the vaccine, it has been investigated to administer the influenza vaccine to the skin upper section as a target site, in which immunocompetent cells are abundant. It will be noted that the skin upper section indicates the epidermis and dermis of the skin.

The skin upper section contains abundant elastic fiber tissues such as elastin, collagen and the like and is harder than the subcutis. Accordingly, the administration into the skin upper section needs a higher injection pressure than the administration into the subcutis because a high back pressure is caused to generate at the skin upper section upon drug injection. It is to be noted that a back pressure generating upon drug injection into the skin upper section according to the Mantoux method using an ordinary syringe is at about 0.8 to 1.5 MPa.

A technique of administering a drug in the body may be one as described in Patent Document 1. The syringe described in Patent Document 1 includes a capsule having a drug solution filled therein, a syringe body, and a piston rod. The piston rod is operated so as to permit the drug solution filled in the capsule to be injected into the body via an injection needle of the syringe body.

The technique of increasing an injection pressure upon drug administration in the body may be one as described in Patent Document 2. The pressure syringe described in Patent Document 2 includes a nozzle having a drug solution chamber, a piston (piston rod), and a release button. The piston is moved at high speed by operation of the release button to generate a high pressure, resulting in the injection, into the body, of the drug solution filled in the drug solution chamber via an injection needle provided at the nozzle.

PRIOR ART DOCUMENTS

Patent Documents

Patent Document 1: Japanese Patent Laid-Open No. Hei 07-246237
Patent Document 2: Japanese Patent Laid-Open No. 2004-261403

SUMMARY OF THE INVENTION

Problem to be Solved by the Invention

However, where a drug is administered to the skin upper section by use of the syringe device set out in Patent Document 1, a force opposite to the direction of injection is exerted against the drug being administered by the action of a high back pressure generating at the skin upper section. Consequently, the needle comes off from the skin, with the attendant problem that the drug leaks from the skin. Thus, the syringe device described in Patent Document 1 is not suited for the case of drug administration to the skin upper section.

On the other hand, with the pressure syringe set out in Patent Document 2, it is necessary to move the piston at high speed so as to generate a high pressure. This requires a specific type of device made up of a release button, a piston rod and a compression spring, with a problem in that the number of parts increases. In this way, the pressure syringe described in Patent Document 2 has a problem in that its constitution becomes complicated.

An amount of a drug that can be administered to the skin upper section is about 100 μL. Where a drug is administered in such a small amount, a small-sized syringe having a small fluid chamber is employed. However, unlike the Mantoux method, a high injection pressure is needed in case where administration to the skin is made by vertical puncture. In order to prevent drug leakage, it is necessary to strongly press a syringe against the skin. However, existing small-sized syringes do not have such a structure suited for continuously pressing to the skin by a strong force and have been difficult to use.

The present invention has been made under such circumstances as stated above and has for its object provision of a drug administration device of a simple constitution that allows a small amount of a drug to be administered to the skin upper section.

Means for Solving Problem

The drug administration device and drug injection device of the present invention are characterized by including a tubular section having a fluid chamber capable of accommodating a drug and a tubular discharge section formed at a tip end thereof, a pusher section having a gasket slidably movable in the fluid chamber and a plunger connected to the gasket, part of which is exposed outside from a base end of the tubular section, a tubular grip section provided outside of the tubular section as kept away from the tubular section, and a connection section connecting the tubular section and the grip section therewith. In this constitution, when a drug is administered to the skin upper section, a user of the drug administration device holds the grip section while touching the connection section with the finger and can operate the pusher section under pressing against the skin. As a consequence, a strong force can be applied to the pusher section, so that a needle does not come off the skin even if a high back pressure occurs at the skin upper section. Thus, the drug leakage from the skin can be prevented.

Effect of the Invention

When using the drug administration device and drug injection device of the invention, the drug can be administered to the skin upper section by use of a simple constitution.

MODE FOR CARRYING OUT THE INVENTION

Figure 1:
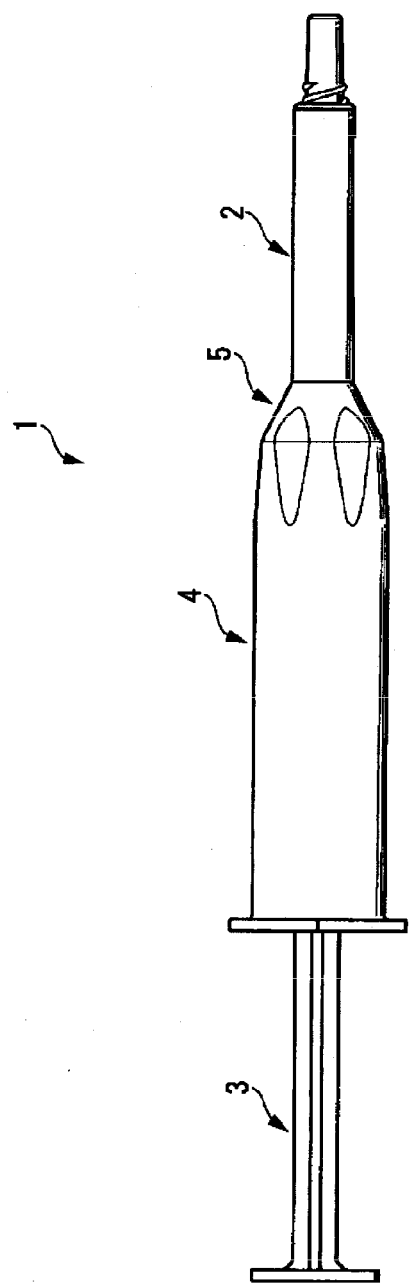
FIG. 1 is a side view embodying a drug administration device of the invention.

Embodiments of the drug administration device of the invention are now described with reference to the accompanying drawings. It will be noted that like members in the respective figures are indicated by like reference numerals.
[Drug Administration Device]

Initially, an embodiment of the drug administration device of the invention is described with reference to FIGS. 1 and 2.

FIG. 1 is a side view of an embodiment of a drug administration device 1. FIG. 2 is an exploded view of an embodiment of the drug administration device 1.

A drug administration device 1 is used in case where a drug is administered to the skin upper section. This drug administration device 1 is made up of a tubular section 2 serving as a syringe filling a drug therein, a pusher member 3 used as a pusher section for discharging the drug filled in the tubular section 2 by application of a compression pressure, a grip section 4 provided along an outer periphery of the tubular section 2 to cover part of the tubular section 2, and a connection section 5 formed at an end portion of the grip section 4 and connecting the tubular section 2 and the grip section 4 therewith.

Figure 2:
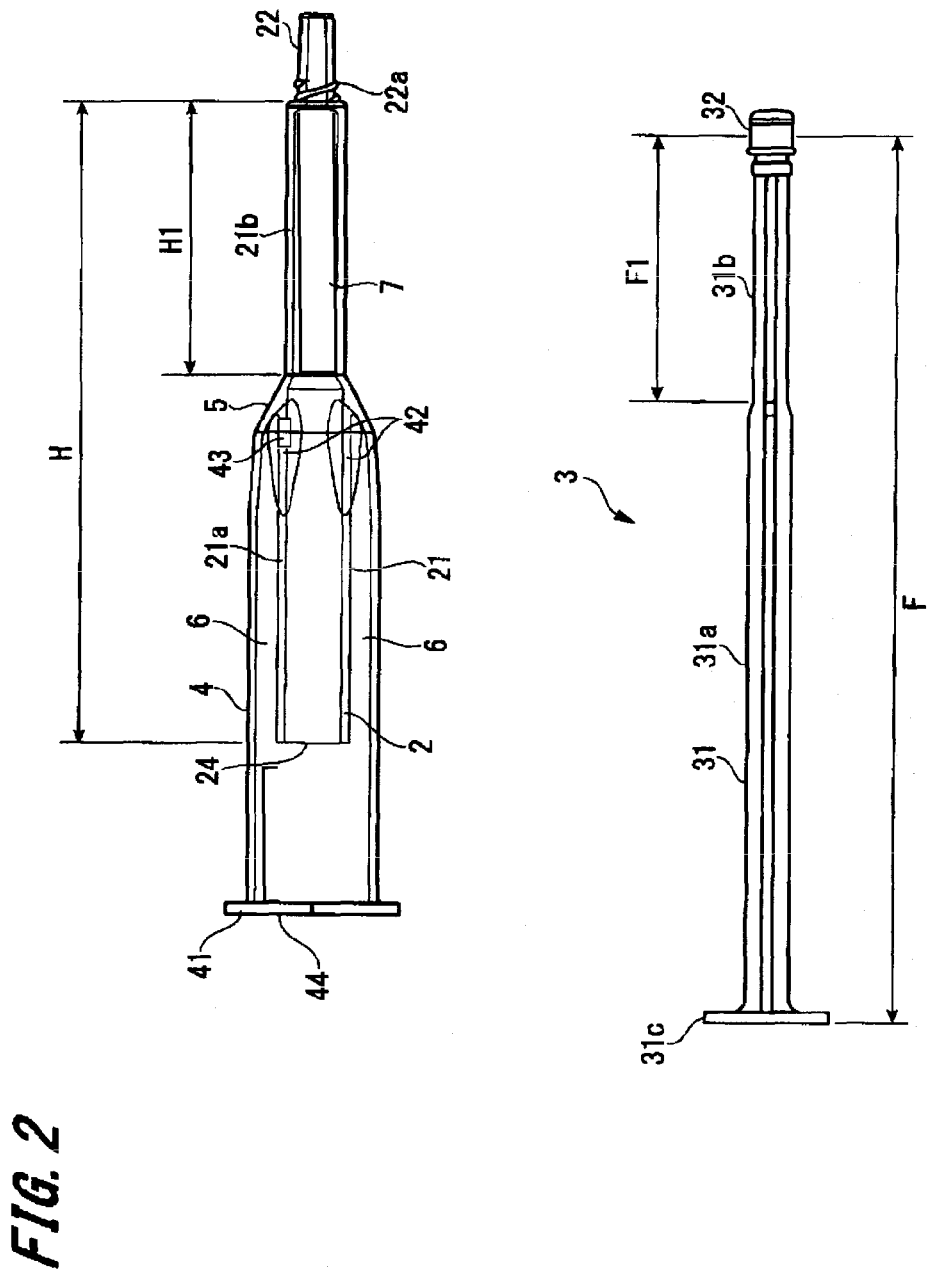
FIG. 2 is an exploded view embodying the drug administration device of the invention.

As shown in FIG. 2, the tubular section 2 includes a tubular body 21 made up of a hollow cylinder having a base end and a tip end, and a discharge section 22 contiguous to the tip end of the tubular body 21. The tubular body 21 is constituted of a covered section 21*a* serving as a second tubular section and covered with the grip section 4 and the connection section 5, an exposed section 21*b* serving as a first tubular section not covered with the grip section 4 and also with the connection section 5 and exposed to outside. In the exposed section 21*b*, there is formed a fluid chamber 7, in which a drug can be stored. The exposed section 21*b* is so formed that its size of the inner diameter is slightly smaller than the size of the inner diameter of the covered section 21*a*. It will be noted that the length of the exposed section 21*b* of the tubular body 21 is indicated as H1 herein.

The discharge section 22 is so formed as to project from the tip end of the tubular body 21 and is made up of a hollow cylinder having an outer diameter that is smaller than the outer diameter of the cylinder of the tubular body 21. This discharge section 22 is so tapered that its diameter is continuously reduced toward the tip end thereof, and is provided with a screw thread 22*a* in the form of a spiral projection around the outer periphery of the discharge section 22. The tubular body 21 has an opening 24 at the base end thereof so as to insert the pusher member 3 therethrough.

The grip section 4 is formed around the outer periphery of the tubular body 21 in the form of a cylinder having an outer diameter larger than the cylinder of the tubular body 21. The inner peripheral surface of the grip section 4 is kept away from the outer peripheral surface of the covered section 21*a* of the tubular body 21 and a space 6 is formed between the grip section 4 and the tubular body 21. This allows the drug administration device 1 to be light in weight. Additionally, the covered section 21*a* can be improved in visibility. More particularly, the grip section 4 is so configured as to cover only the covered section 21*a* therewith and not to cover the exposed section 21*b* of the tubular body 21. This permits an amount of drug in the fluid chamber 7 or the scale provided at the outer peripheral surface of the exposed section 21*b* to become readily visible.

The connection section 5 is formed in the vicinity of the tip end of the grip section 4. The connection section 5 is provided between the tubular body 21 and the grip section 4 so as to connect the grip section 4 and the tubular body 21 therewith. The connection section 5 is continuously formed from the tip end of the grip section 4 to the tip end portion of the covered section 21*a* and becomes a fixed section for fixing the grip section 4 to the periphery of the tubular body 21 at a distance from the space 6. The connection section 5 is so tapered that its outer diameter is continuously reduced along toward the base end portion of the exposed section 21*b*. More particularly, the connection section 5 is formed with an inclined face having a diameter that is smaller than the outer diameter of the grip section 4 and larger than the outer diameter of the tubular body 21. In this way, the connection section 5 is formed with the inclined face so that a contact area between the finger of a user and the connection section 5 is increased. Thus, the user firmly can hold the grip section 4 by wrapping the little finger around the connection section 5.

It is to be noted that although the connection section 5 of this embodiment is formed at the tip end portion of the grip section 4, the position at which the connection section is provided is not specifically limited so far as the position is one at which a user is likely to hold the grip section 4. For instance, it may be formed in the vicinity of an intermediate between the tip end and the base end of the grip section 4. In this case, the grip section 4 is narrowed at the middle thereof. Although the shape of the connection section 5 of this embodiment is in a smoothly tapered form, it may be one on which the finger of a user catches. For example, a stepped shape or a configuration of projections provided on the surface of the grip section may be used.

The grip section 4 is formed at the base end thereof with an opening 44 through which the pusher member 3 is inserted. A flange 41 is formed around the opening 44. An angular portion for preventing the drug administration device 1 from rolling is formed around the flange 41.

A notch 42 is formed at the outer peripheral surface at the tip end side of the grip section 4 across the connection section 5 for preventing the rolling of the drug administration device 1. Plurality (four in the configuration of the figures) of notches 42 is disposed at equal intervals along the periphery of the grip section 4.

The notch 42 is formed by cutting off part of the outer peripheral surface of the grip section 4 and has a planar portion. The planar portion of the notch 42 is formed with a gate 43 for injecting a molding resin. More particularly, the planar portion is more recessed than the surface of the cylinder of the grip section 4, so that an influence of burrs of the gate 43 occurring after molding can be suppressed.

The tubular section 2, grip section 4 and connection section 5 of the drug administration device 1 are integrally molded. Nevertheless, for example, the grip section 4 may be molded as a separate member and fixedly secured to the tubular section 2 by use of a bonding agent or the like.

As materials for the tubular body 21, grip section 4 and connection section 5, there may be used synthetic resins (plastics) such as polycarbonates, polypropylene, polyethylene and the like. Alternatively, metals such as stainless steels, aluminum and the like may also be used.

As shown in FIG. 2, the pusher member 3 is provided with a rod-shaped plunger 31 and a gasket 32 attached to the tip end of the plunger 31. The plunger 31 is formed at the base end thereof with a disk-shaped flange 31c. The flange 31c has a diameter that is larger than an inner diameter of the cylinder of the grip section 4. A user presses the flange 31c with the thumb, whereupon the pusher member 3 is moved and the drug filled in the fluid chamber 7 of the drug administration device 1 is discharged to outside.

The plunger 31 is so formed that its section is cruciform and has a large-diameter section 31a provided at the base end side and having a large diameter and a small-diameter section 31b provided at the tip end side and having a small diameter. A gasket 32 is attached to the side of the small-diameter section 31b. The small-diameter section 31b is so formed that its length F1 is slightly larger than a length H1 of the exposed section 21b of the tubular body 21.

In this way, the plunger 31 is made thin at the tip end side thereof, so that it can be readily inserted into the opening 24 of the tubular body 21. Since the plunger 31 is made larger in diameter at the base end side where not inserted into and supported with the exposed section 21b thereby keeping the strength of the plunger 31, the plunger 31 can be prevented from being broken during operation. If the plunger 31 undergoes deflection during operation, the large-diameter section 31a comes into contact with the inner surface of the covered section 21a, thereby preventing the plunger 31 from bending in excess. Moreover, the covered section 21a has an adequate length and the outer diameter of the exposed section 21b is set larger than the inner diameter of the covered section 21a, so that there is a reduced possibility that the discharge section 22 enters into the inner cavity of a grip section 4 of another drug administration device 1 to be stuck therein. This enables troubles during transport or fixing to tools to be reduced and lowering in productivity in the production process to be prevented. In addition, a space between the covered section 21a and the grip section 4 is set smaller than the outer diameter of the discharge section 22, thereby showing similar effects as set out above.

It will be noted that the plunger 31 of this embodiment is configured to have a shaft diameter of 4 to 5 mm and an axial length of 105 mm. In this configuration, the plunger is more elongated than with the case of ordinary drug administration devices.

As a material for the plunger 31, there may be used synthetic resins (plastics) such as polystyrene, polycarbonates, polypropylene, polyethylene and the like. Alternatively, there may also be used metals such as stainless steels, aluminum and the like.

Figure 3:
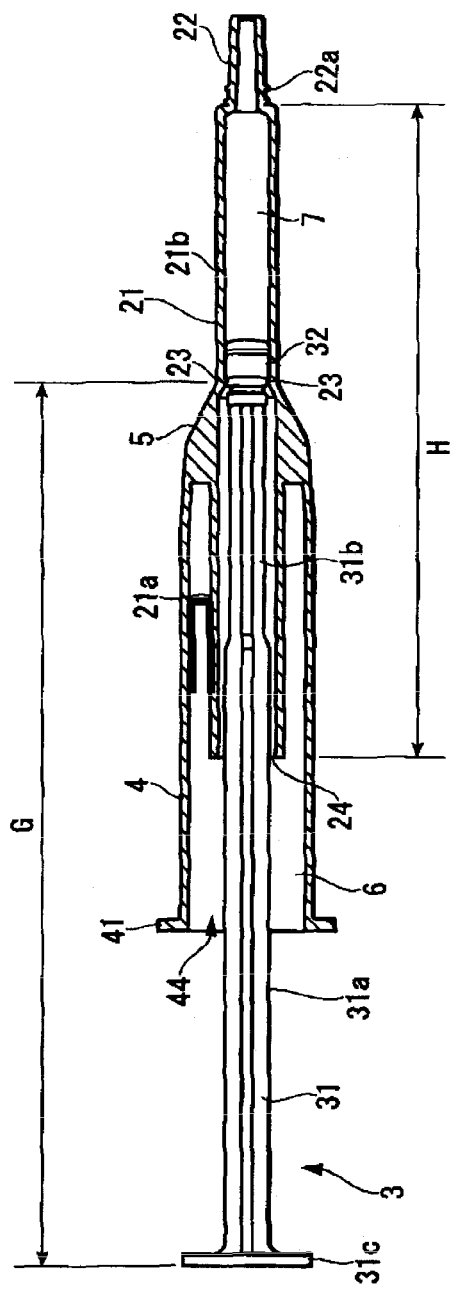
FIG. 3 is a sectional view embodying the drug administration device of the invention.

FIG. 3 is a sectional view of an embodiment of a drug administration device 1.

As shown in FIG. 3, a tubular body 21 slidably accommodates therein a gasket 32 connected to a plunger 31. A space in an exposed section 21b of the tubular body 21 is liquid-tightly partitioned with the gasket 32, thereby forming a fluid chamber 7 accommodating a drug therein.

At a base end portion of the exposed section 21b inside the tubular body 21, there is provided a stopping portion 23 for stopping the gasket 32. The stopping portion 23 is shaped in the form of a ring by causing part of the inner wall of the tubular body 21 to be inwardly protruded. It will be noted that the stopping portion 23 should be so configured as to narrow the diameter of the tubular body 21. This allows the gasket 32 to be stopped with the stopping portion 23, so that when a drug is filled in the fluid chamber 7, it can be inhibited to withdraw a pusher member 3 from the tubular body 21 by mistake. The stopping portion is not limited to one integrally molded with the tubular body 21 as in this embodiment, but may be formed as a separate member, such as a seal, fixedly secured to the inner side of the tubular body.

The stopping portion 23 for stopping the gasket 32 therewith is disposed in the vicinity of a boundary between a covered section 21a and the exposed section 21b of the tubular body 21 at a side of the exposed section 21b. Accordingly, the fluid chamber 7 can be formed in the exposed section 21b that is ready to be visually observed from outside. Thus, a user can discharge the drug under operation of the pusher member 3 while visually observing an amount of the drug filled in the fluid chamber 7 without interruption with the grip section 4.

In this embodiment, the stopping portion 23 is provided in the vicinity of the connection section 5. This permits a distance G from the connection section 5 to a flange 31c of the pusher member 3 to be substantially equal to a length F of the pusher member 3 in a state that the gasket 32 is stopped with the stopping portion 23. Accordingly, if the length F of the pusher member 3 is set at an appropriate value, a user can set a range where the flange 31c can be pushed with the thumb in a state of touching the little finger on the connection section 5 even in the case of a drug being filled in the fluid chamber 7 to a full extent.

The tubular body 21 of the embodiment is formed to have a diameter of 7 mm. This diameter is substantially equal to an outer diameter of an ordinary small-capacity syringe of 0.5 mL or 1.0 mL. However, with such an ordinary small-capacity syringe, when a drug is administered into the skin upper section, a difficulty is involved in holding the syringe against a high back pressure because of the small outer diameter. On the other hand, with the drug administration device 1 of the invention having the grip section 4 whose diameter is larger than the tubular body 21, a user can hold the grip section 4 sufficiently to push it to the skin against the back pressure.

As shown in FIG. 3, the plunger 31 of the pusher member 3 of this embodiment is so configured to be appreciably small in diameter relative to its length. Accordingly, in order to stably support the pusher member 3 during operation, it is necessary to form a portion of the tubular body 21 accommodating the pusher member 3 as being elongated to some extent. In this embodiment, while the pusher member 3 has the length F of 105 mm, the length H of the tubular body 21 including a combination of the covered section 21a and the exposed section 21b is formed at 72 mm. This enables the pusher member 3 not to be shaken during operation and thus, a user is able to operate the pusher member 3 in a stable condition.

[Manner of Using the Drug Administration Device]

The gasket 32 is connected to the tip end of the plunger 31 and the space within the tubular body 21 is liquid-tightly partitioned by means of the gasket 32 thereby forming the fluid chamber 7. The base end of the plunger 31 projects from the opening 24 of the tubular body 21 and also from the opening 44 of the grip section 4. A user holds the grip section 4 to operate the plunger 31 of the pusher member 3, under which while keeping the state where the little finger of the user hangs on the connection section 5, the flange 31c of the plunger 31 projecting from the opening 44 of the grip section 4 is pushed in with the thumb toward the tip end direction. This permits the gasket 32 to be axially moved inside the tubular body 21 to cause the drug filled in the fluid chamber 7 to be discharged. At this time, the user manipulates the connection section 5 in a state of the little finger hangs thereon. Thus, the drug administration device 1 can be easily operated with one hand.

[Drug Injection Device]

Next, a drug injection device 8 using an injection needle assembly 100 is now described with reference to FIG. 4.

Figure 4:
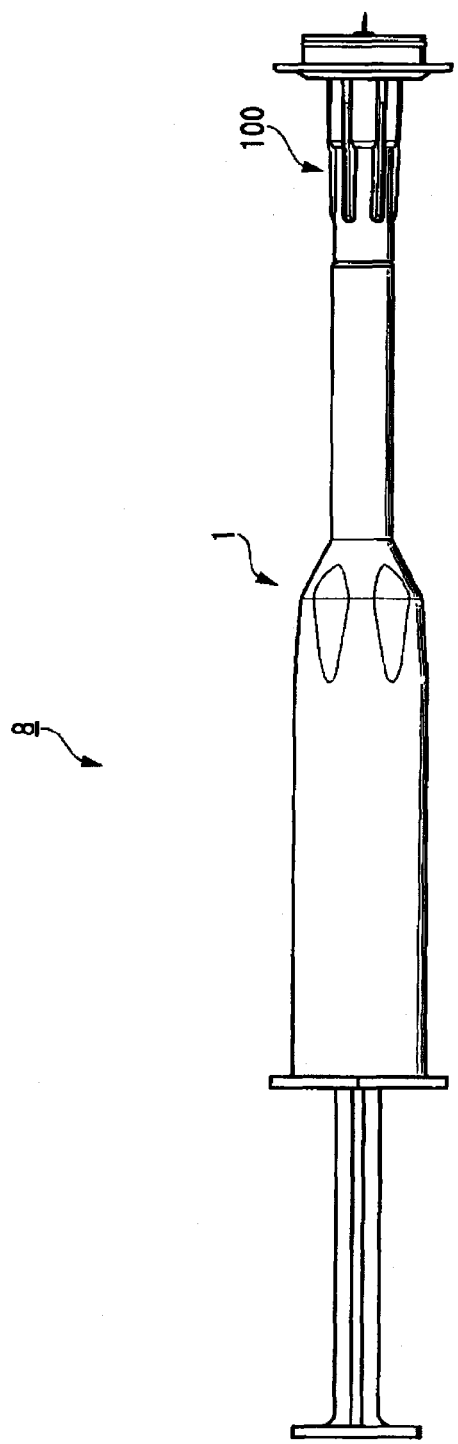
FIG. 4 is a side view embodying a drug injection device of the invention.

FIG. 4 is a side view of the case where an injection needle assembly 100 is mounted to a drug administration device 1 to provide a drug injection device 8.

As shown in FIG. 4, the drug injection device 8 is assembled by mounting the injection needle assembly 100 to the drug administration device 1. For the mounting of the injection needle assembly 100 to the drug administration device 1, the discharge section 22 of the tubular section 2 is inserted into a fitted portion 132 (see FIG. 7) of the injection needle assembly 100. A screw thread 22a made on the discharge section 22 is fitted in a thread groove 135 of the fitted portion 132. In this way, the mounting of the injection needle assembly 100 to the drug administration device 1 is completed.

It will be noted that in this embodiment, although the drug injection device 8 is assembled by mounting the injection needle assembly 100 to the drug administration device 1, a needle tube may be directly mounted to the drug administration device 1 for use as a drug injection device.

[Injection Needle Assembly]

Figure 5:
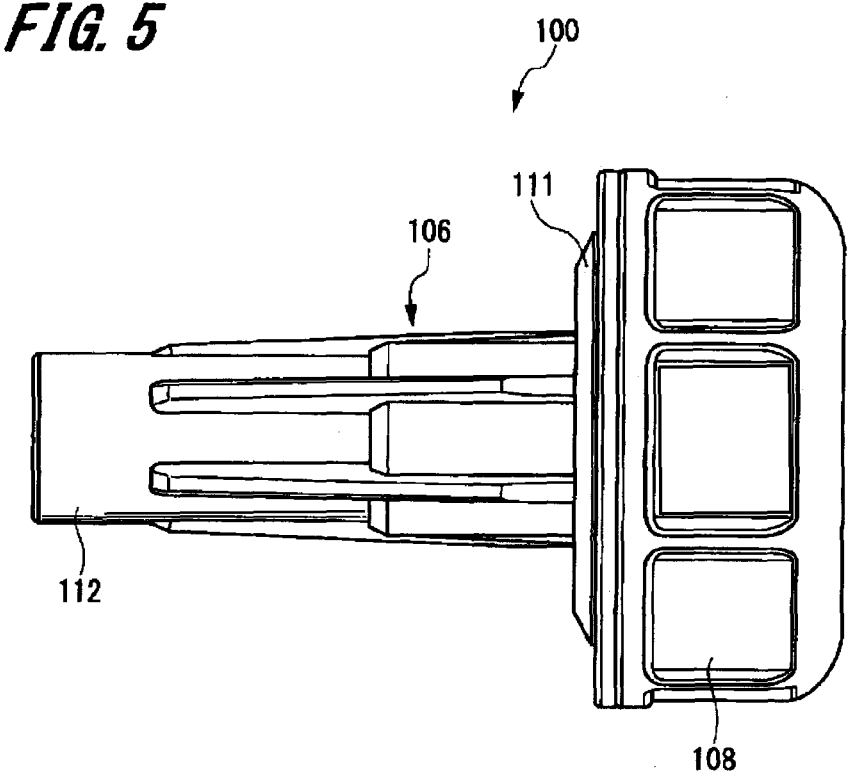
FIG. 5 is a side view of an injection needle assembly used in the drug injection device of the invention.

The injection needle assembly 100 mounted to the drug administration device 1 is now described with reference to FIGS. 5 to 7. It will be noted that like members in the respective figures are indicated by like reference numerals.

Figure 6:
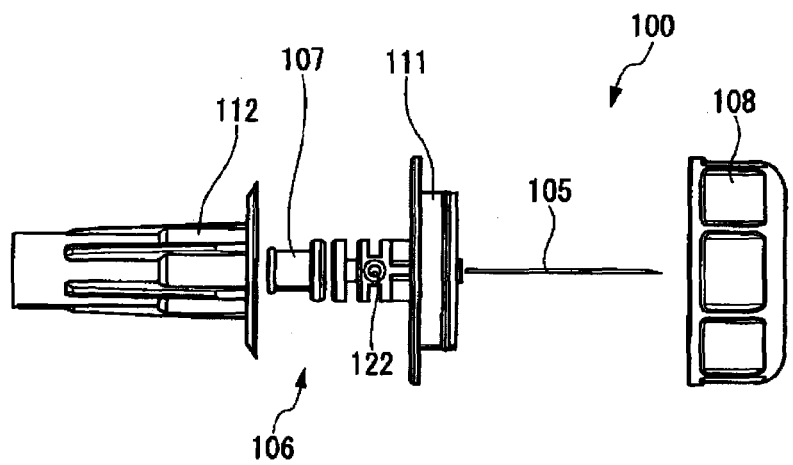
FIG. 6 is an exploded view of the injection needle assembly used in the drug injection device of the invention.

As shown in FIG. 6, the injection needle assembly 100 used as a needle holder member mounted to the tubular section 2 includes a hollow needle tube 105 having a needle hole, a needle hub 106 to which the needle tube 105 is fixed, a resilient member 107 located within the needle hub 106, and a cap 108 detachably attached to the needle hub 106. The needle hub 106 includes a first member 111 holding the needle tube 105 and a second member 112, into which the discharge section 22 of the tubular section 2 described hereinafter is fitted.

The needle tube 105 of the injection needle assembly 100 used may be one that has a size of 26 to 33 gauge (outer diameter: 0.2 to 0.45 mm), preferably 30 to 33 gauge, based on the ISO standards for medical needle tube (ISO9626:1991/Amd. 1:2001(E)).

The needle tube 105 is provided at one end thereof with a needle tip 105A having a blade face 105a. The other end of the needle tube 105 that is an opposite side relative to the needle tip 105A is called "base end 105B" hereinafter. The axial length of the needle tube 105 in the blade face 105a (hereinafter referred to as "bevel length B") may be not larger than 1.4 mm (adult) that is a smallest thickness of the skin upper section described hereinafter and not less than about 0.5 mm that is a bevel length when a short bevel is formed in the 33-gauge needle tube. That is, the bevel length B is preferably set within a range of 0.5 to 1.4 mm.

Further, the bevel length B is more preferably not larger than 0.9 mm (child) that is a smallest thickness of the skin upper section, i.e. a more preferred bevel length B is within a range of 0.5 to 0.9 mm. It will be noted that the short bevel means a blade face that is ordinarily employed in injection needles and is made at 18 to 25° to the axial direction of the needle.

The materials for the needle tube 105 include, for example, stainless steels although not limited thereto. Other types of metals including aluminum, aluminum alloys, titanium and titanium alloys may also be used. As the needle tube 105, there may be used not only a straight needle, but also a tapered needle at least a part of which is tapered. The tapered needle may be one wherein its base end portion has a diameter larger than the tip end portion and the intermediate portion has a tapered structure. The sectional shape along the radial direction of the needle tube 105 may be not only circular, but also polygonal such as triangular.

Next, the needle hub 106 is now described. Although the first member 111 and the second member 112 of the needle hub 106 are formed as a separate member, they may be formed integrally. The materials for the first member 111 and the second member 112 include synthetic resins (plastics) such as polycarbonates, polypropylene, polyethylene and the like.

The first member 111 includes a base portion 115, a control portion 116, a stabilizing portion 117 and a guide portion 118. The base portion 115 is formed substantially in the form of a column and has axially vertical end faces 115a, 115b. The end face 115a is formed at a tip end of the base portion 115 and the end face 115b is formed at a rear end of the based portion 115.

The control portion 116 is provided at the center of the end face 115b of the base portion 115 and is made up of a columnar projecting portion projecting in an axial direction of the base portion 115. An axis of the control portion 116 is coincident with an axis of the base portion 115.

At the axes of the base portion 115 and the control portion 116, there is provided a through hole 121, through which the needle tube 105 passes. The base portion 115 is provided with an injection hole 122 (see FIG. 6) for injecting a bonding agent 120 (see FIG. 7) into the through hole 121. This injection hole 122 is opened at an outer peripheral surface of the base portion 115 and communicates with the through hole 121. More particularly, the needle tube 105 is fixed to the base portion 115 by means of the bonding agent 120 injected from the injection hole 122 into the through hole 121.

The base end 105B of the needle tube 105 is arranged to project from the end face 115b of the base portion 115. The base portion 115 is inserted from the side of the end face 115b into the second member 112 and the needle tube 105 is passed into a through hole 145, described hereinafter, of the resilient member 107 at the side of the base end 105B thereof. The end face 115b of the base portion 115 comes in contact with an end face 141a, described hereinafter, of the resilient member 107.

A connection piece 124 is provided at the outer peripheral surface of the base portion 115. This connection piece 124 is formed as a ring-shaped flange projecting in a radial outer direction of the base portion 115 and has plain faces 124a, 124b facing in an axial direction of the base portion 115. The second member 112 is connected and fixed to the plain face 124b of the connection piece 124. The end portion of the connection piece 124 serves as a guide portion 118. This guide portion 118 will be described in detail hereinafter.

The end face of the control portion 116 forms a needle protrusion surface 116a, at which a needle tip 105A of the needle tube 105 projects. The needle protrusion surface 116a is formed as a plain face axially intersecting at right angles with the needle tube 105. This needle protrusion surface 116a regulates a depth of a puncture of the needle tube 105 after contact with the skin surface when the needle tube 105 is punctured into the skin upper section. More particularly, the depth of the puncture of the needle tube 105 into the skin upper section is determined by a length (hereinafter referred to as "projection length L") of the needle tube 105 projecting from the needle protrusion surface 116a.

The thickness of the skin upper section corresponds to a depth of from the skin surface to the dermis layer and is generally within a range of 0.5 to 3.0 mm. Accordingly, the projection length L of the needle tube 105 can be set within a range of 0.5 to 3.0 mm.

By the way, a vaccine is usually administered to the brachial region. With the administration to the skin upper section, the administration site is preferably a region around the shoulder, particularly, the deltoid muscle region, at which the skin is thick. 19 children and 31 adults were subjected to measurement of the thickness of the skin upper section of the deltoid muscles. This measurement was made by use of an ultrasonic measuring device (NP60R-UBM, high-resolution echo imaging device for small animals, Nepa Gene Co., Ltd.) for imaging the skin upper section whose ultrasonic reflectivity is high. It will be noted that the measurements had a logarithmic normal distribution and a range of MEAN±2SD was determined by geometric average.

As a result, the thickness of the skin upper section in the deltoid muscles of the children was found to be at 0.9 to 1.6 mm. The thickness of the skin upper section in the deltoid muscles of the adults was found to be at 1.4 to 2.6 mm for the distal portion, at 1.4 to 2.5 mm for the central portion and at 1.5 to 2.5 mm for the proximal portion. In view of the above, it was confirmed that the thickness of the skin upper section in the deltoid muscles was at not less than 0.9 mm for children and at not less than 1.4 mm for adults. Accordingly, for the injection into the skin upper section of the deltoid muscles, it is preferred to set the projection length L of the needle tube 105 within a range of 0.9 to 1.4 mm.

When the projection length L is so set as defined above, it becomes possible to reliably place the blade face 105a of the needle tip 105A at the skin upper section. Consequently, if the needle hole (drug discharge port) opened at the blade face 105a is positioned at any portion of the blade face 105a, it can be arrived to the skin upper section. It will be noted that even if the drug discharge port is located in the skin upper section, the needle tip 105A, punctured too deeply into the skin upper section, causes a drug to be seeped under a subcutaneous portion from a space between the side face of the tip end portion of the needle tip 105A and the cut skin. To avoid this, it is important that the blade face 105a be reliably located in the skin upper section.

It will be noted that with a needle tube that is thicker than 26 gauge, it is difficult to make the bevel length B at not larger than 1.0 mm. Accordingly, in order to set the projection length L of the needle tube 105 within a preferred range (of 0.9 to 1.4 mm), the use of a needle tube that is thinner than 26 gauge is preferred.

The needle protrusion surface 116a is so formed that a distance S from the peripheral edge to the outer peripheral surface of the needle tube 105 is not larger than 1.4 mm, preferably within a range of 0.3 to 1.4 mm. The distance S from the peripheral edge of the needle protrusion surface 116a to the peripheral surface of the needle tube 105 is set while taking it into consideration that a pressure is exerted on vesicles formed by administrating a drug to the skin upper section. That is, the needle protrusion surface 116a is so set that it is much smaller than the vesicles formed in the skin upper section and has a size enough not to impede the formation of the vesicles. As a consequence, when the needle protrusion surface 116a presses the skin around the needle tube 105, leakage of a drug being administered can be prevented.

The stabilizing portion 117 is cylindrically formed as projecting from the plain surface 124a of the connection piece 124 provided at the base portion 115. The stabilizing portion 117 has the needle tube 105 and the control portion 116 arranged in the cylindrical hallow thereof. In other words, the stabilizing portion 117 is cylindrically formed to cover therearound the control portion 116, through which the needle tube 105 is inserted and which is kept away from the needle tip 105A of the needle tube 105 in the radial outer direction.

The cap 108 is detachably fitted in the stabilizing portion 117. This cap 108 covers the needle tip 105A of the needle tube 105. Hence, where the needle hub 106 is mounted to the drug administration device 1, the needle tip 105A can be prevented from touching with the finger and the like of a user. When the cap is re-mounted after use, a once used drug injection device 8 or injection needle assembly 100 can be invariably kept in a safe condition. Thus, a user is able to subject the used drug administration device 8 or injection needle assembly 100 to waste treatment or the like in a worry-free way.

Figure 7:
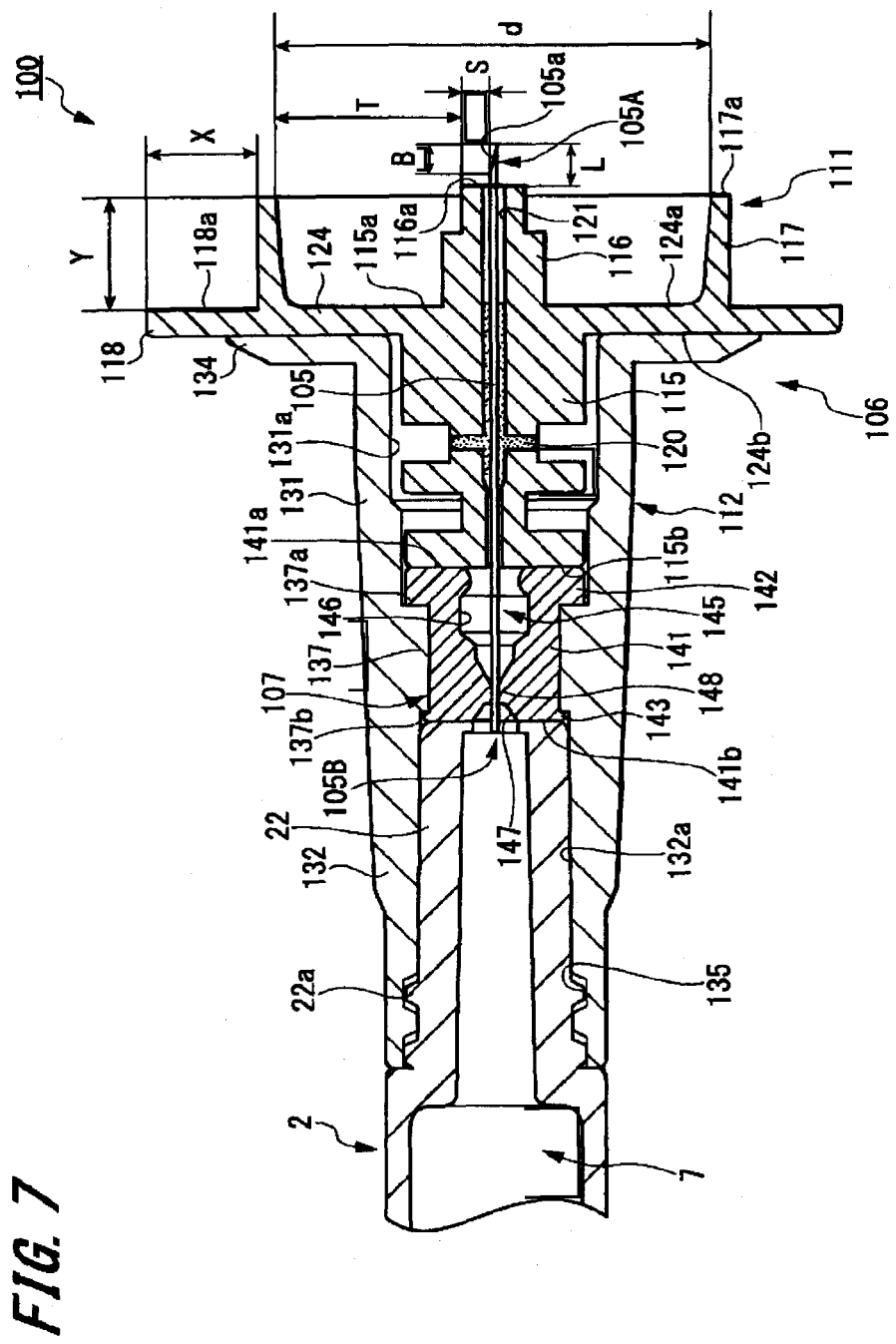
FIG. 7 is a sectional view of the injection needle assembly used in the drug injection device of the invention.

As shown in FIG. 7, an end face 117a of the stabilizing portion 117 is situated nearer to a side of the base end 105B of the needle tube 105 than the needle protrusion surface 116a of the control portion 116. When the needle tip 105A of the needle tube 105 is punctured in a living body, the needle injection surface 116a initially contacts the skin surface, followed by contacting the end face 117a of the stabilizing portion 117. At this time, since the end face 117a of the stabilizing portion 117 contacts the skin, the drug injection device 8 is stabilized and the needle tube 105 can be held in a posture substantially vertical to the skin.

It will be noted that if the end face 117a of the stabilizing portion 117 is situated on the same plain surface as the needle protrusion surface 116a or is situated nearer to a side of the needle tip 105A of the needle tube 105 than the needle protrusion surface 116a, the needle tube 105 may be kept in a posture substantially vertical to the skin. It will also be noted that when the elevation of the skin is taken into account under pressing of the stabilizing portion 117 against the skin, it is preferred that the axial distance between the end face 117a of the stabilizing portion 117 and the needle protrusion surface 116a is set at not larger than 1.3 mm.

Furthermore, an inner diameter d of the stabilizing portion 117 is set equal to or larger than the diameter of vesicles formed in the skin. More particularly, a distance T from the inner wall surface of the stabilizing portion 117 to the peripheral edge of the needle protrusion surface 116a is set within a range of 4 mm to 15 mm. This can prevent vesicle formation from being inhibited due to the application of a pressure to the vesicles from the end face 117a of the stabilizing portion 117.

The distance T from the inner wall surface of the stabilizing portion 117 to the peripheral edge of the needle protrusion surface 116a has no upper limit so far as it is not less than 4 mm. However, a larger distance T results in a larger outer diameter of the stabilizing portion 117. Accordingly, where a slender arm such as of a child is punctured with the needle tube 105, it becomes difficult to bring the entire end face 117a of the stabilizing portion 117 into contact with the skin. In this sense, it is preferred to regulate the distance T at 15 mm in maximum while taking the slenderness of child's arm into account.

If a distance S from the peripheral edge of the needle protrusion surface 116a to the outer peripheral surface of the needle tube 105 is not less than 0.3 mm, the control portion 116 does not stick into the skin. Accordingly, when taking the distance T (not less than 4 mm) of from the inner wall surface of the stabilizing portion 117 to the peripheral edge of the needle protrusion surface 116a and the diameter (about 0.3 mm) of the needle tube 105 into consideration, an inner diameter d of the stabilizing portion 117 can be set at not less than 9 mm.

It will be noted that the shape of the stabilizing portion 117 is not limited to the cylinder, but may be formed as a horn-shaped cylinder, such as a quadratic prism, a hexagonal column or the like, having a cylindrical hallow at the center thereof.

The guide portion 118 is a portion located at an outer peripheral side than the stabilizing portion 117 disposed on the connection piece 124. This guide portion 118 has a contact face 118a that contacts the skin. The contact face 118a is part of a plain surface 124a of the connection piece 124 and is a plain surface substantially parallel to the end face 117a of the stabilizing portion 117. When the stabilizing portion 117 is pushed until the contact face 118a of the guide portion 118 contacts the skin, a pressing force of the stabilizing portion 117 and the needle tube 105 against the skin can be secured invariably at not less than a given value. Thus, the skin is reliably punctured therein with a portion protruding from the needle protrusion surface 116a (corresponding to the protrusion length L) of the needle tube 105, thereby preventing a drug from leaking during the administration.

A distance Y from the contact face 118a of the guide portion 118 to the end face 117a of the stabilizing portion 117 (hereinafter referred to as "guide portion height") is so set that its length allows the skin to be pressed and punctured with the needle tube 105 and the stabilizing portion 117 at an appropriate pressing force. In doing so, the pressing force of the needle tube 105 and the stabilizing portion 117 against the skin is guided by the guide portion 118, so that not only the needle tip 105A (blade face 105a) of the needle tube 105 can be reliably situated at the skin upper section, but also a user can feel a sense of security. It should be noted that an appropriate pressing force of the needle tube 105 and the stabilizing portion 117 is, for example, at 3 to 20 N.

While the inner diameter d of the stabilizing portion 117 is preferably within a range of 11 to 14 mm, the guide portion height Y is appropriately determined based on a length X of from the end face of the guide portion 118 to the outer peripheral surface of the stabilizing portion 117 (hereinafter referred as "guide portion length"). For instance, if the inner diameter d of the stabilizing portion 117 is 12 mm and the guide portion length X is 3 mm, the guide portion height Y is set within a range of 2.3 to 6.6 mm.

Next, the second member 112 is described. The second member 112 is formed substantially in a tubular form. One end portion along the axial direction of the second member 112 becomes an inserted portion 131, into which the base portion 115 of the first member 111 is inserted, and the other end portion becomes a fitted portion 132, in which the discharge section 22 of the tubular section 2 is fitted. A tubular hole 131a of the inserted portion 131 is so set in size as to correspond to the base portion 115 of the first member 111.

The inserted portion 131 is provided with a fixing piece 134 fixed to the connection piece 124 of the first member 111. This fixing piece 134 is formed as a radially projecting ring-shaped flange contiguous to the tip end of the inserted portion 131. The fixing piece 134 is in abutment with the plain surface 124b of the connection piece 124 of the first member 111 and is fixedly secured. For the manner of fixing between the fixing piece 134 and the connection piece 124, mention can be made, for example, of the use of a bonding agent, ultrasonic melt welding, laser welding, a fixation screw and the like.

A tubular hole 132a of the fitted portion 132 is set in size correspondingly to the discharge section 22 of the tubular section 2 and is continuously made smaller in size toward the side of the inserted portion 131. The fitted portion 132 is formed, on the inner surface thereof, with a screw groove 135 to be threadly engaged with the screw thread 22a of the discharge section 22 of the tubular section 2.

An engaging protrusion 137 engaging with the resilient member 107 is formed between the inserted portion 131 and the fitted portion 132. This engaging protrusion portion 137 is formed as a step projecting in the radial inner direction from the inner surface of the second member 112 and has engaging faces 137a, 137b that are axially intersected substantially at right angles. The engaging surface 137a of the engaging protrusion portion 137 is engaged with a flange portion 142, described hereinafter, of the resilient member 107. The engaging surface 137b is engaged with a stopper projection 143 of the resilient member 107.

Next, the resilient member 107 is described. The resilient member 107 is situated within the second member 112 of the needle hub 106 and is disposed between the first member 111 and the discharge section 22 of the tubular section 2. This resilient member 107 has a body portion 141, the flange portion 142 disposed at one end of the body portion 141 in its axial direction, and the stopper projection 143 disposed at the other end of the body portion 141.

The body portion 141 is formed substantially in a cylindrical form and has end faces 141a, 141b vertical to the axial direction. The end face 141a of the body portion 141 is in abutment with the end face 115b of the base portion 115 of the first member 111, and the end face 141b is in liquid-tight abutment with a tip end of the discharge section 22 disposed at the tubular section 2. That is, the end face 141b is an abutment face, with which the tip end of the discharge section 22 is in light-tight abutment.

The body portion 141 is provided with a though hole 145, into which the base end 105B of the needle tube 105 projecting from the end face 115b of the base portion 115 is inserted. This through hole 145 extends along the axial direction of the body portion 141 and is opened at the end faces 141a, 141b. The inner surface of the body portion 141 is made up of an end face side spaced portion 146, an abutment face side spaced portion 147 and a contact portion 148.

The end face side spaced portion 146 forms an opening of the though hole 145 in the end face 141a. The end face side spaced portion 146 is spaced from the outer peripheral surface of the needle tube 105 and is so tapered that the diameter of the through hole 145 continuously increases toward the end face 141a. In doing so, the base end 105B of the needle tube 105 projecting from the end face 115b of the base portion 115 is able to easily pass through the through hole 145. It will be noted that the shape of the end face side spaced portion 146 in the through hole 145 is not limited to the tapered one so far as it allows easy passage of the needle tube 105 through the through hole 145.

The abutment face side spaced portion 147 forms an opening of the through hole 145 in the end face (abutment face) 141b. The abutment face side spaced portion 147 is spaced from the outer periphery surface of the needle tube 105 and is tapered in such a way that the diameter of the through hole 145 continuously increases toward the end face 141b. When the abutment face side spaced portion 147 is formed in the resilient member 107, it can be prevented to cover the base end 105B of the needle tube 105 with the end face 141b of the body portion 141 after having been elastically deformed.

The contact portion 148 is formed between the end face side spaced portion 146 and the abutment face side spaced portion 147. This contact portion 148 liquid-tightly contacts with the outer peripheral surface of the needle tube 105. This can prevent a drug in the tubular section 2 from infiltrating between the needle tube 105 and the resilient member 107 and leaking toward the side of the first member 111 of the needle hub 106.

The flange portion 142 is formed as a ring projecting from the outer peripheral surface of the body portion 141 in the radial outer direction. The outer diameter of the flange portion 142 is substantially equal to the outer diameter of the base portion 115 of the first member 111. One of the plain surfaces of the flange portion 142 abuts with the engaging surface 137a of the engaging protrusion portion 137 provided in the second member 112, and the other plain surface abuts with the end face 115b of the base portion 115 of the first member 111. The resilient member 107 is attached to the needle hub 106 by sandwiching the flange portion 142 between the engaging protrusion portion 137 of the second member 112 and the base portion 115 of the first member 111.

The stopper projection 143 is formed, like the flange portion 142, in the form of a ring projecting from the outer peripheral surface of the body portion 141 in the radial outer direction. This stopper projection 143 engages with the engaging surface 137b of the engaging protrusion portion 137 disposed in the second member 112. The axial movement of the resilient member 107 is prevented by engagement of the flange portion 142 and the stopper projection 143 with the engaging protrusion portion 137 of the second member 112.

As a material for the resilient member 107, mention is made of elastic materials including various types of rubber materials such as natural rubber, silicone rubber and the like, various types of thermoplastic elastomers such as polyurethanes, styrene elastomers, or mixtures thereof.

It will be noted that although the injection needle assembly 100 is exemplified and illustrated in this embodiment, the type of injection needle assembly is not limited thereto. For instance, the invention may also be applied to an injection needle assembly of a simple structure wherein a needle tip is projected from the needle hub only to a length sufficient to arrive at the skin upper section.

[Manner of Use of the Drug Injection Device]

Next, the manner of use of the drug injection device 8 is described. In order to puncture the needle tip 105A of the needle tube 105 into a living body, the end face 117a of the stabilizing portion 117 is initially made faced to the skin. This permits the needle tip 105A of the needle tube 105 to be faced to the skin to be punctured. Next, the drug injection device 8 is moved substantially vertically to the skin to puncture the needle tip 105A into the skin, and the end face 117a of the stabilizing portion 117 is pressed against the skin. At this time, the needle protrusion surface 116a contacts the skin to enable the skin to be flatly deformed, so that the needle tip 105 side of the needle tube 105 can be punctured into the skin only by the projection length L.

Next, the end face 117a of the stabilizing portion 117 is pressed until the contact face 118a of the guide portion 118 contacts the skin. The guide portion height Y (see FIG. 7) is so set in length that the skin is punctured under an appropriate pressing force of the needle tube 105 and the stabilizing portion 117. Accordingly, a force of pressing the skin with the stabilizing portion 117 becomes a given value.

As a result, an appropriate pressing force of the stabilizing portion 117 can be recognized by a user and thus, the blade face 105a and the needle tip 105A of the needle tube 105 can be reliably situated in the skin upper section thereby permitting a drug to be stably injected. In this manner, the guide portion 118 serves as a mark of giving recognition of an appropriate pressing force of the stabilizing portion 117, so that a user makes use of the drug injection device 8 without worry.

Further, the stabilizing portion 117 abuts with the skin and thus, the drug injection device 8 is stabilized in posture, so that the needle tube 105 can be punctured straightly into the skin. Displacement of the needle tube 105 as would occur after puncture can be prevented, thereby ensuring stable administration of a drug. Moreover, with a needle tube whose projection length is, for example, as very short as about 0.5 mm, there may be some cases that when the needle tip, abutted to the skin, is not punctured into the skin. In this connection, however, when the skin pressed with the stabilizing portion 117 is vertically pushed down, the skin at the inner side of the stabilizing portion 117 is pulled to create a state of the skin exerted thereon with a tension. In this condition, a difficulty is involved in escaping of the skin from the needle tip 105A of the needle tube 105. Accordingly, an effect of easier puncture of the needle tip 105A into the skin can be expected by the provision of the stabilizing portion 117.

After the puncture of the needle tip 105A of the needle tube 105 into the skin, the plunger 31 is pressed down to move the gasket 32 toward the side of the discharge section 22. This enables the drug filled in the fluid chamber 7 of the tubular section 2 to be forced out of the discharge section 22 and injected from the needle tip 105A via the needle hole of the needle tube 105 into the skin upper section.

At this time, the injection needle assembly 100 is mounted to the drug administration device 1. With drug injection device 8 of this embodiment, while a user keeps the little finger touched on the connection section 5 of the drug administration device 1, the grip section 4 can be held to press the flange portion 31c of the plunger 31 with the thumb. This enables a strong force to be added to the skin in one hand. Thus, if a high back pressure occurs when the drug is administered to the upper tissues, the needle cannot be removed from the skin, thereby inhibiting the drug from leaking from the skin upper section.

It will be noted that the drug administration device and the drug injection device of the invention are not limited to those embodiments stated hereinabove. With respect to the length of the tubular body 21, the diameter and length of the plunger, the types of materials and the configurations may be variously varied and altered without departing from the scope of the invention.

EXPLANATIONS OF LETTERS OR NUMERALS

1: Drug administration device, 2: Tubular section, 3: Pusher member, 4: Grip section, 5: Connection section, 6: Space, 7: Fluid chamber, 8: Drug injection device, 21: Tubular body, 21a: Covered portion (Second tubular portion), 21b: Exposed portion (first tubular portion), 22: Discharge section, 22a: Screw thread, 23: Stopping portion, 24: Opening, 31: Plunger, 31c: Flange, 32: Gasket, 41: Flange, 42: Notch, 43: Gate, 44: Opening, 100: Injection needle assembly, 105: Needle tube, 105A: Needle tip, 105B: Base end, 105a: Blade face, 106: Needle hub, 107: Resilient member, 108: Cap, 111: First member, 112: Second member, 115:

Base portion, 116: Control portion, 116a: Needle protrusion surface, 117: Stabilizing portion, 118: Guide portion, 120: Bonding agent, 121: Through hole, 124: Connection piece, 131: Inserted portion, 132: Fitted portion, 134: Fixing piece, 135: Thread groove, 137: Engaging protrusion portion, 141: Body portion, 141a: End face, 141b: End face (abutment face), 142: Flange portion, 143: Stopper projection, 145: Through hole, 146: End face side spaced portion, 147: Abutment face side spaced portion,
148: Contact portion,
F: Length of pusher member
F1: Length of small-diameter section
G: Distance from connection section to plunger flange
H: Length of tubular body
H1: Length of exposed portion

What is claimed is:

1. A drug administration device comprising:
    a tubular section having a fluid chamber capable of accommodating a drug therein and a tubular discharge section formed at a tip end thereof;
    a pusher section having a gasket slidably movable within said fluid chamber and a plunger which is connected to said gasket and part of which is exposed outside from a base end of said tubular section;
    a tubular grip section disposed outside of said tubular section and kept away from said tubular section; and
    a connection section connecting said tubular section and said grip section; and
    said tubular section includes a first tubular portion wherein said fluid chamber is formed and a second tubular portion disposed contiguously from a base end of said first tubular portion, said grip section is disposed not to cover said first tubular portion but to cover at least part of said second tubular portion,
    said tubular section, said grip section and said connection section are integrally molded, and
    said first tubular portion has on the inner surface thereof a stopping portion for stopping said gasket, and said stopping portion is disposed in the vicinity of said connection section,
    said stopping portion for stopping the gasket is disposed in the vicinity of a boundary between a covered section of said first tubular portion where said grip section does not cover and an exposed section of said second tubular portion where said grip covers, and is disposed at a side of the exposed section, so that when said drug is filled in said fluid chamber, it is inhibited to withdraw said pusher section from said first tubular portion.

2. The drug administration device as defined in claim 1, characterized in that an inner diameter of said first tubular portion is formed smaller than an inner diameter of said second tubular portion.

3. The drug administration device as defined in claim 2, characterized in that said plunger is so formed that the diameter on the tip end side is smaller than the diameter on the base end side.

4. The drug administration device as defined in claim 1, characterized in that a base end of said second tubular portion is formed not to be exposed from a base end of said grip section.

5. The drug administration device as defined in claim 1, characterized in that said grip section has at least one notch on an outer peripheral portion at a tip end side thereof.

6. The drug administration device as defined in claim 1, characterized in that said discharge section has a screw thread at a base end side of the peripheral surface thereof.

7. A drug injection device comprising:
    a tubular section having a fluid chamber capable of accommodating a drug therein and a cylindrical discharge section formed at a tip end thereof;
    an injection needle including a needle tube having a needle tip and a needle hub for retaining said needle tube and attached to said discharge section;
    a pusher section having a gasket slidably moving within said fluid chamber and a plunger which is connected to said gasket and part of which is exposed outside from a base end of said tubular section;
    a tubular grip section disposed outside of said tubular section and kept away from said tubular section; and
    a connection section connecting between said tubular section and said grip section; and
    said tubular section includes a first tubular portion wherein said fluid chamber is formed and a second tubular portion disposed contiguously from a base end of said first tubular portion, said grip section is disposed not to cover said first tubular portion but to cover at least part of said second tubular portion,
    said tubular section, said grip section and said connection section are integrally molded, and
    said first tubular portion has on the inner surface thereof a stopping portion for stopping said gasket, and said stopping portion is disposed in the vicinity of said connection section
    said stopping portion for stopping the gasket is disposed in the vicinity of a boundary between a covered section of said first tubular portion where said grip covers, and is disposed at a side of the exposed section, so that when said drug is filled in said fluid chamber, it is inhibited to withdraw said pusher section from said first tubular portion.

8. The drug injection device as defined in claim 7, characterized in that a base end of said second tubular portion is formed not to be exposed from a base end of said grip section.

9. The drug injection device as defined in claim 7, characterized in that said first tubular portion has on the inner surface thereof a stopping portion for stopping said gasket, and said stopping portion is disposed in the vicinity of said connection section.

10. The drug injection device as defined in claim 7, characterized in that said grip section has at least one notch on an outer peripheral portion at a tip end side thereof.

11. The drug injection device as defined in claim 7, characterized in that said discharge section has a screw thread at a base end side of the peripheral surface thereof.

* * * * *